United States Patent [19]

Mault

[11] Patent Number: 5,038,792

[45] Date of Patent: * Aug. 13, 1991

[54] OXYGEN CONSUMPTION METER

[76] Inventor: James R. Mault, 4227 Pin Oak Dr., Durham, N.C. 27707

[*] Notice: The portion of the term of this patent subsequent to Apr. 17, 2007 has been disclaimed.

[21] Appl. No.: 368,947

[22] Filed: Jun. 23, 1989

Related U.S. Application Data

[63] Continuation-in-part of Ser. No. 213,184, Jun. 29, 1988, Pat. No. 491,108.

[51] Int. Cl.⁵ .............................................. A61B 5/08
[52] U.S. Cl. .................................... 128/718; 128/719; 128/725
[58] Field of Search ............... 128/716, 718, 719, 725, 128/726, 430, 205.12, 205.23, 205.24, 203.26, 204.17, 201.13; 73/861, 861.02, 861.03, 198, 200

[56] References Cited

U.S. PATENT DOCUMENTS

| | | | |
|---|---|---|---|
| 3,799,149 | 3/1974 | Rummel et al. | 128/718 |
| 3,895,630 | 7/1975 | Bachman | 128/718 |
| 4,211,239 | 7/1980 | Raemer et al. | 128/718 |
| 4,359,057 | 11/1982 | Manzella | 128/718 |
| 4,444,201 | 4/1984 | Itoh | 128/204.23 |
| 4,572,208 | 2/1986 | Cutler et al. | 128/718 |
| 4,619,269 | 10/1986 | Cutler et al. | 128/718 |
| 4,753,245 | 6/1988 | Gedeon | 128/718 |
| 4,917,108 | 4/1990 | Mault | 128/718 |

Primary Examiner—Randall L. Green
Assistant Examiner—K. Reichle
Attorney, Agent, or Firm—Krass & Young

[57] ABSTRACT

An indirect calorimeter for calculating the metabolic rate of a subject by measuring the oxygen consumption during respiration over a period of time includes a gas flow meter providing output electric signals to a microprocessor which drives a display and printer. A carbon dioxide scrubber is connected to the flow meter and a mouthpiece so that inhaled gas passes first through the scrubber and then through the flow meter before being provided to the subject's respiratory system through the mouthpiece. The exhaled gas passes through the scrubber and then through the flow meter. The difference in volume between the inhaled gas and the exhaled gas is proportional to the oxygen consumption of the subject and the microprocessor integrates that signal over the time of the test, and multiplies it by a constant to provide a metabolic rate display. By passing both the inhaled and exhaled gases through the scrubber before their volume is measured, their temperature and humidity are modified to a state of equal temperature and humidity.

5 Claims, 3 Drawing Sheets

OXYGEN CONSUMPTION METER

CROSS-REFERENCE TO RELATED APPLICATION

This application is a continuation-in-part of application Ser. No. 213,184 filed June 29, 1988, now U.S. Pat. No. 4,917,108.

FIELD OF THE INVENTION

This invention relates to indirect calorimeters for measuring metabolic rate on the basis of respiratory oxygen consumption and more particularly to such a calorimeter which scrubs the $CO_2$ from the exhaled gas and computes the difference between the inhaled gas volume and the volume of the scrubbed exhaled gas to calculate oxygen consumption.

BACKGROUND OF THE INVENTION

Measurement of the energy expenditure of humans is important for a number of reasons. For nutritional purposes measurement of the resting energy expenditure is important to a determination of the proper caloric content for feedings of hospitalized patients in view of the fact that certain diseases and traumas may cause the resting energy expenditure to vary substantially from normal values. In burn patients the metabolic rate may increase by as much as 300%. Other hospital situations in which the measurement of rate of metabolic oxygen consumption is important include the adjustment of parental feedings for infants, and the control of respiratory gases during surgical operations. The resting energy expenditure may also decrease substantially in the course of a weight loss diet, and knowledge of this basal energy requirement is important to the adjustment of caloric inputs in order to achieve a target loss. Similarly, knowledge of caloric consumption during exercise is useful for cardiac rehabilitation and athletic training.

A variety of indirect calorimeters for measuring oxygen consumption during respiration have been devised and are available commercially. These broadly include closed circuit devices wherein oxygen depleted during respiration is replenished from an oxygen source and the volume of replenishing oxygen is measured to determine respiratory oxygen consumption. A device of this type is disclosed in U.S. Pat. No. 4,753,245. Open circuit devices generally measure the volume of inhaled gas and the proportions of carbon dioxide and oxygen in exhaled gas to determine the respiratory oxygen consumption. Devices of this class are disclosed in U.S. Pat. Nos. 3,523,529, 4,619,269, 4,221,224 and 4,572,208.

All of these devices are relatively complex and expensive and require specially trained technicians for their operation. Their use has largely been limited to hospital settings for the adjustment of nutritional requirements for critically ill patients in intensive care units.

A potentially simpler and less expensive form of calorimeter would measure the inhaled gas volume, pass the exhaled gas over a carbon dioxide scrubber to remove the lung contributed $CO_2$ from the exhaled gas and then measure the remaining gas volume. The difference between the two measured volumes would be a direct function of the respiratory oxygen consumption. However, because the exhaled gas has substantially different temperature and water vapor content than the inhaled gas, the volume measurements may grossly misestimate the actual oxygen consumption. Additionally, because such a device would measure variations in the relatively small differential between two large measurements, design of the device to attain a reasonable accuracy presents a problem.

SUMMARY OF THE INVENTION

The present invention is accordingly directed toward a simple and low cost indirect calorimeter, or oxygen consumption meter that overcomes the deficiencies of the prior art and may be used by relatively untrained personnel so that it is adapted to use in a wide variety of situations for measurement of oxygen consumption and energy expenditure. The calorimeter of the present invention can operate from atmospheric air or any other oxygen source, such as a mechanical ventilator, and utilizes a chemical carbon dioxide scrubber, and inhaled and exhaled air volume flow meter means. The scrubber, the flow meter, a source of gas to be inhaled and a respiratory connector such as a mask, endotracheal tube or mouthpiece are interconnected with conduits and one-way valves so that inhaled air passes through the scrubber before its volume is measured and is then passed to the mouthpiece, and exhaled air similarly passes through the scrubber before its volume is measured.

As the exhaled air passes through the scrubber, the chemical reaction between carbon dioxide and the absorber substance for example, ($CO_2 + NaOH = + H_2O + Salt$) raises the temperature and water vapor content of the scrubber. Using one-way valves, the inhaled and exhaled breaths are directed through the scrubber before their respective volumes are measured. After a short period of operation the inhaled and exhaled air will have substantially the same temperature and water vapor content so that their volumes, as measured by the flow sensor, may be directly compared without the need for temperature/water vapor measurement adjustment.

The flow meter means preferably provides pulsed signals with each electric pulse representing an increment of flow volume, and the system includes a microprocessor-based computation and display unit which receives the pulse signals, distinguishes inhalations from exhalations, and generates integrals of their differences over a period of time. The microprocessor preferably stores these integrated different signals for short periods of time representing increments of use of the calorimeter during the test and at the conclusion of the test displays the value representing the oxygen consumption over the latter portion of the test, multiplied by a constant to arrive at the display of kilocalories per 24 hour time. This arrangement discards the initial readings which may be inaccurate until the scrubber chemicals have built up a stable temperature and water vapor level. The integration of a large number of respiration cycles minimizes error resulting from limited repeatability of the flow sensor.

A preferred embodiment of the invention, which will subsequently disclosed in detail, employs a single flow meter for measuring both the inhaled and exhaled volume, thereby eliminating a possible differential of accuracy between separate meters as an error source. The flow meter, which is preferably of the turbine type, but may take other forms such as ultrasonic or electromagnetic meters, is connected to receive the gas output from the scrubber. Conduits and one-way valves connect the mouthpiece to both the inlet of the scrubber and the output of the flow meter. When the user inhales, atmospheric air or air from a mechanical respirator ventilator is drawn into the scrubber, through the flow meter, to the mouthpiece or other patient interface. Exhaled air passes through the scrubber and the flow meter to the atmosphere or back to the ventilator. The microprocessor analyzes the train of pulses it receives from the flow meter to distinguish inhalations from exhalations based on the integrated volume of each breath since the exhaled air will have a lower volume than the inhaled air since it loses more carbon dioxide to the scrubber. In an alternative embodiment, the system includes a flow direction sensor disposed in one of the conduits and connected to the microprocessor so that the microprocessor can distinguish inhalations and exhalations from the flow direction of the air that passes over the direction sensor.

The present calorimeter may also be used in positive pressure ventilation systems using any concentration of oxygen source. This includes intensive care mechanical ventilators and closed loop anesthesia. The present invention may also be applied to exercise stress testing.

In an alternative embodiment of the invention separate flow sensors may be provided for the inhaled and exhaled volume, eliminating the need for the microprocessor to distinguish pulse trains associated with the inhaled and exhaled breaths.

The device of the present invention is thus simple, inexpensive, easy to use, and has excellent accuracy.

BRIEF DESCRIPTION OF THE DRAWINGS

Other objectives, advantages, and applications of the present invention will be made apparent by the following detailed description of a preferred embodiment of the invention. The description makes reference to the accompanying drawings in which.

DETAILED DESCRIPTION OF THE PREFERRED EMBODIMENT

Figure 1:
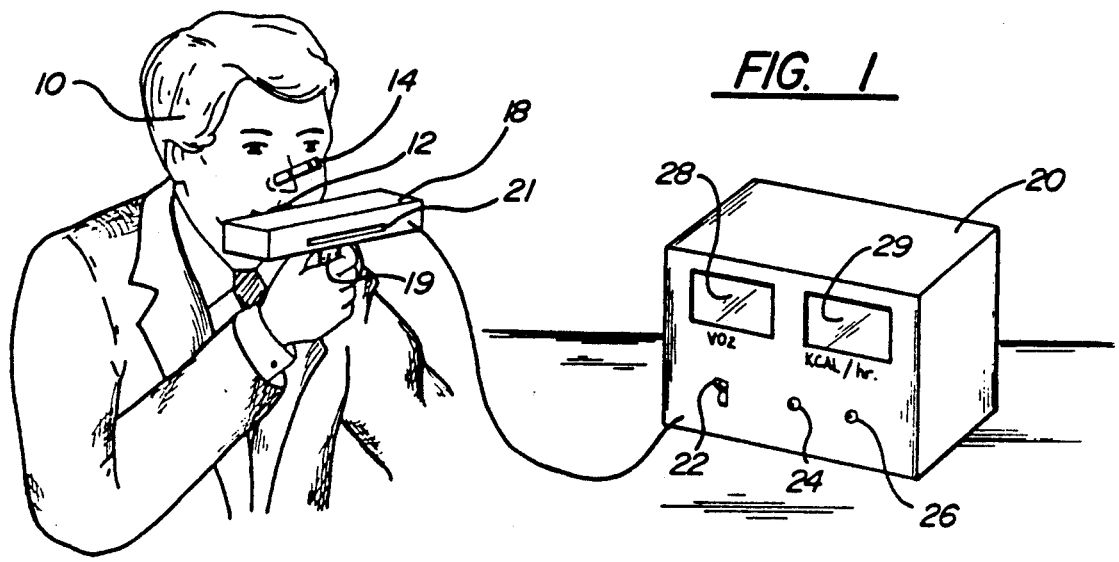
FIG. 1 is a perspective view of the preferred embodiment of the indirect respiratory calorimeter of the present invention being used by a subject.

FIG. 1 illustrates the preferred embodiment of the present invention in use. A user 10 inhales and exhales air from and into a user respiratory interface taking the form of a mouthpiece 12 adapted to engage the inner surfaces of the user's mouth so as to form the sole passage for inhaled and exhaled air passing through the mouth. A nose clamp 14 of conventional construction may be employed in connection with the mouthpiece 12 to assure that all respiratory air passes through the mouthpiece. In alternative configurations a mask that engages the nose as well as the mouth might be employed. In embodiments such as those illustrated in FIGS. 6 and 7, intended for use with mechanical ventilators, an endotracheal tube may be employed rather than a mouthpiece or mask.

The mouthpiece 12 is directly connected to a small instrument housing 18 that is manually held by a handle 19 fixed to the housing. The instrument housing 18 contains the other components of the system and is connected to a microprocessor-based computation and display unit 20. The unit 20 includes an ON/OFF switch 22 and a pair of LED signal lights 24 and 26. The signal light 24 is illuminated when the switch is first thrown to the ON position to indicate that the test is underway. At the end of a predetermined time, the light 24 is extinguished and the signal light 26 is illuminated, signaling that enough time has elapsed and that the subject may quit at any time. In the preferred embodiment of the present invention, the housing 18 and the mouthpiece 12 are intended for one use and are disposable.

The unit 20 also includes a first digital display 28 which displays the value $VO_2$, the volume of inspired oxygen consumed per minute, and a second display 29 which exhibits the value of Kcal/24 hours, i.e., the value arrived at by multiplying the integral of the difference between the scrubbed inhaled volume and the scrubbed exhaled volume by a constant.

Figure 2:
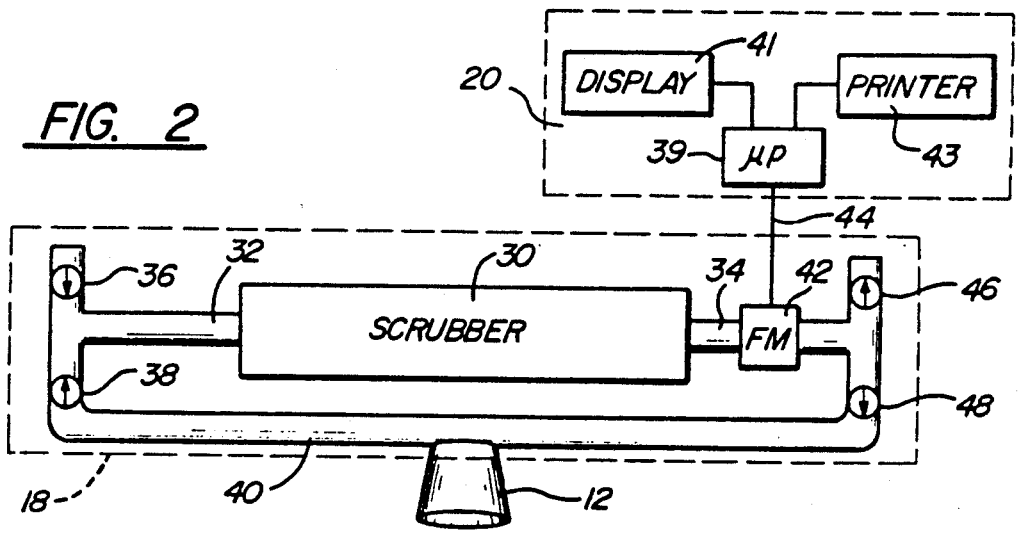
FIG. 2 is a schematic illustration of the gas flow circuitry of the embodiment of FIG. 1.

FIG. 2 provides a schematic of the circuitry in the instrument housing 18 of the preferred embodiment. The housing includes a carbon dioxide scrubber 30. The scrubber 30 is a container having an inlet and an outlet and a central passageway filled with a carbon dioxide absorbent material such as sodium hydroxide or calcium hydroxide. Such absorbers are well-known to the art. Sometimes they include sodium hydroxide and calcium hydroxide admixed with silica in a form known as soda lime. Another absorbent material used is "Baralyme" which comprises a mixture of barium hydroxide and calcium hydroxide.

Preferably the scrubber 30 employs a carbon dioxide absorbent media in the form of a fiber structure in which there is absorbed and retained in liquid a solution of one or more substances capable of chemically binding carbon dioxide, such as aqueous sodium hydroxide solution.

The scrubber 30 becomes saturated with $CO_2$ after some period of use. The preferred embodiment of the present invention uses a small scrubber 30. In an alternative embodiment, the instrument housing 18 of FIG. 1 is of a table top configuration and utilizes a large scrubber 30 that has a longer useful life. In this embodiment, the scrubber is preferably removable from said system so that after becoming saturated, a user may replace it with a new scrubber cartridge. In this table top configuration, the mouthpiece is also removably attached to the system. The microprocessor unit 20 of this embodiment may further include means for keeping track of the number of uses of the scrubber and indicating to the user when it should be replaced.

The circuitry in the instrument housing 18 further includes conduits 32 and 34 connected to the inlet and outlet of the scrubber 30, respectively. The opposite end of the conduit 32 is also connected to two one-way valves 36 and 38. One-way valve 36 allows the passage of air from the atmosphere into conduit 32. One-way valve 38 is connected to one end of another conduit 40 that is directly connected to a mouthpiece 12. The valve 38 allows for air exhaled into the mouthpiece to pass into conduit 32.

Conduit 34 is connected to a flow meter 42, of the turbine type, that measures the volume of air passing through it. Such flow meters are well known in the art. In the preferred embodiment, the flow meter is removably attached to the system so that the housing 18 and the mouthpiece 12 may be disposed of after usage, while the flow meter is retained. An opening in the instrument housing, indicated at 21 in FIG. 1, functions to allow the user to connect and disconnect a flow meter to the system. The flow meter may be calibrated by providing a known volume of gas to the system and analyzing the number of pulses generated by the flow meter.

The flow meter 42 is connected to the microprocessor unit 20 via a connection wire 44. The meter 42 provides the microprocessor unit with pulsed signals, each electric pulse representing an increment of flow volume. The microprocessor unit 20 includes a microprocessor 39 connected to a display 41 and, in the preferred embodiment, a printer 43. The microprocessor functions to distinguish pulse signals representing inhalations and exhalations by categorizing alternate volume flows, representing inhalations or exhalations, together, and to generate integrals of their differences over a period of time. In the preferred embodiment, the microprocessor stores the integrated signals for short periods of time representing increments of use of the calorimeter during the test. At the conclusion of the test, the microprocessor sums the values representing the oxygen consumption over the latter portion of the test, and multiplies this by a constant to arrive at the display of kilocalories/24 hours.

Figure 5:
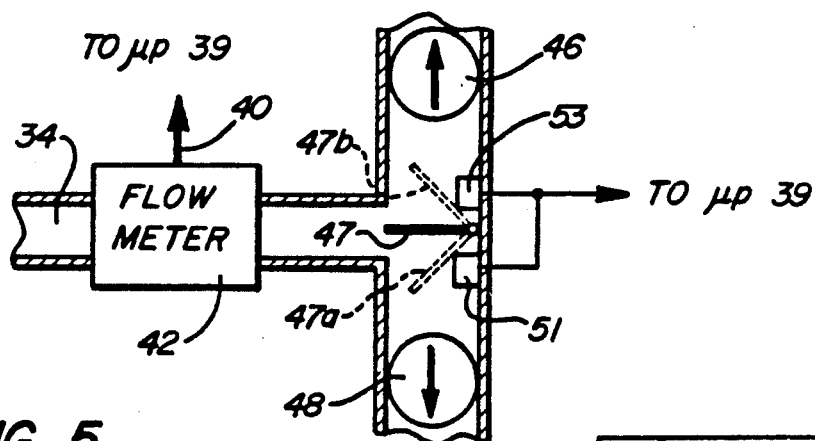
FIG. 5 is a partial schematic view of a section of an alternative construction of a single flow meter indirect calorimeter of the type illustrated in FIG. 2 but incorporating a mechanical sensor for flow direction to generate an electric signal distinguishing flow associated with exhalations from flows representative of inhalations.

The end of the flow meter 42 opposite the end connected to conduit 34 is connected to two one-way valves 46 and 48. Valve 46 allows exhaled air passing through the flow meter to exit to the atmosphere. Valve 48 is connected to the other end of the conduit 40 and allows inspired air that has passed through flow meter 42 to enter conduit 40 and exit through the mouthpiece 12. In an alternative embodiment, illustrated in detail in FIG. 5, a flow direction sensor may be disposed between valves 46 and 48 and connected to the microprocessor in order to more accurately distinguish between inhalations and exhalations. Such a sensor may comprise a lightweight resilient flap 47 having one end fixed to the conduit wall between the valves 46 and 48 so that in the absence of flow it extends normally across the conduit. When the user breathes the resultant air flow moves the free end of the flap 47 to one of two different positions depending on whether air is exiting through valve 46 on an exhale, or passing through valve 48 on an inhale. These alternative positions are illustrated by phantom lines 47a and 47b. Two contact sensors 51 and 53 are used to sense the position of the flap and provide signals to the microprocessor.

Alternatively, the flow direction could be sensed by directional switches (not shown) integrated with the undirected valves 36, 38, 46 or 48.

The mouthpiece 12 is directly connected to the conduit 40 and allows a subject to breathe air into and out of the conduit. The system functions as follows: When a user inhales through mouthpiece 12, atmospheric air is drawn into valve 36, through conduit 32, through the scrubber 30, into conduit 34, through the flow meter 42, into valve 48, through conduit 40, to the mouthpiece 12 and into the lungs of the user. Exhaled air passes through the mouthpiece, into conduit 40, through valve 38, into conduit 32, through the scrubber 30 and the flow meter 42, exiting through valve 46 to the atmosphere. The conduits and valves used in the instrument housing 18 are well known to the art and are preferably very short in length in order to minimize the error created by extraneous air in the conduits and valves.

Figure 3:
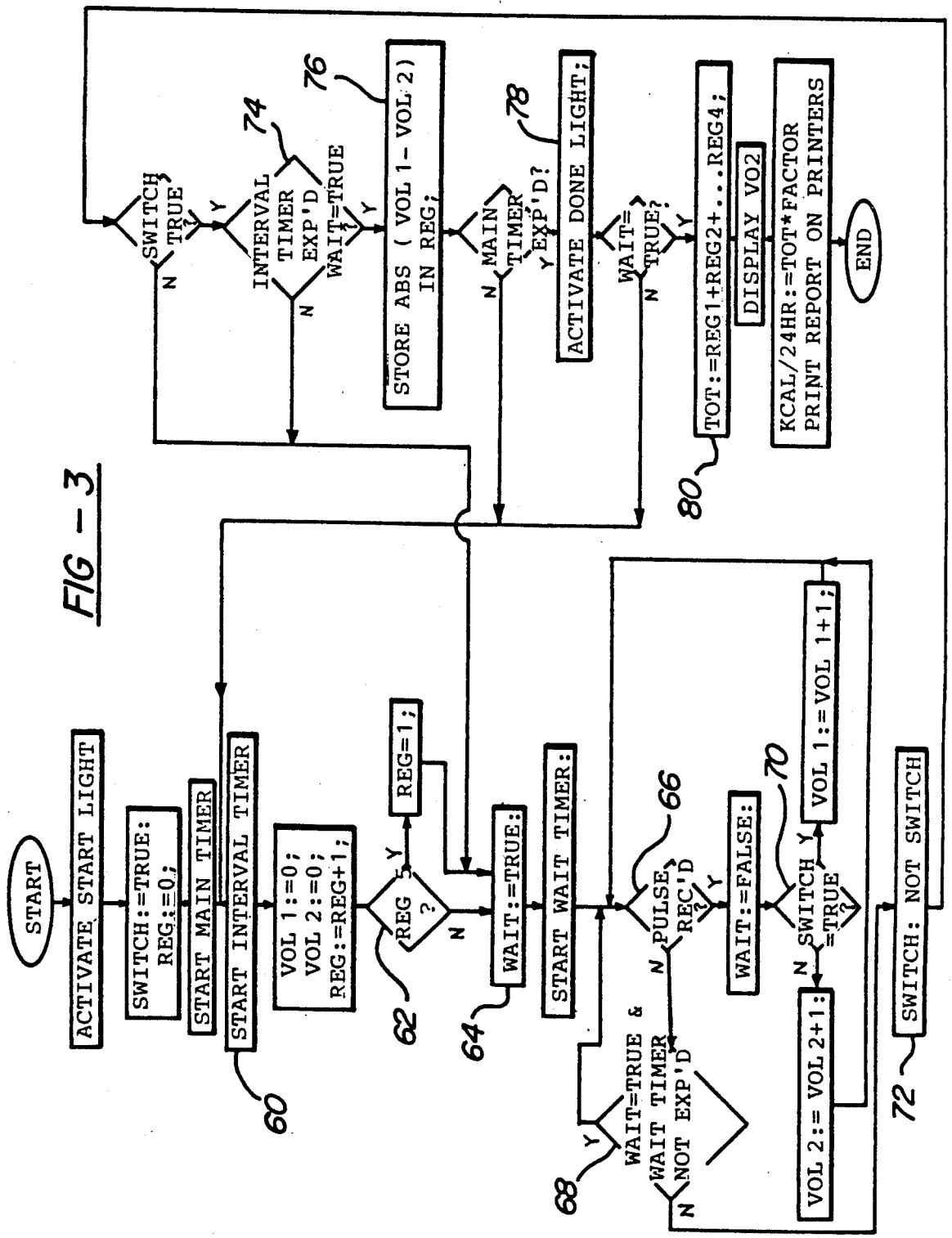
FIG. 3 is a flow diagram illustrating the manner of operation of the microprocessor used with the present invention.

FIG. 3 provides a flow diagram illustrating the general flow of operation of the microprocessor in the preferred embodiment of the present invention. The algorithm uses five registers to store values of integrals of the volumes as generated by the flow meter 42 during five successive intervals.

First, the LED signal light 24 of FIG. 1 is illuminated in order to indicate to the user that the test is underway. The boolean variable SWITCH is then initialized to true and the integer variable REG, for keeping track of the current register in use, is initialized to 0.

Next, the main timer is started. This timer expires after the minimum time required for the test has passed. In the preferred embodiment, this time is 10 minutes.

Next, at the step indicated at 60, an interval timer is started. This timer keeps track of short increments of the total time. In the preferred embodiment this time is 1 minute. The microprocessor finds the integrated difference between the exhaled and inhaled gas volumes for each increment of time and stores these values at memory locations designated REG 1, REG 2. . . . The processor only stores the most recent 5 periods, so that the initial readings that may be inaccurate due to temperature differences between the inhaled and exhaled gas are discarded. Next, the counter variables Vol 1 and Vol 2 are initialized to 0, and REG is incremented by one. At 62 a check is made as to whether the current register is greater than 5. If not, the algorithm goes to the step indicated at 64. If REG>5, then REG is set back to 1 and the algorithm continues at step 64.

At 64, the boolean variable WAIT is set to true. This variable is used to indicate whether the microprocessor is waiting for a pulse signal from the flow meter. Next, a wait timer is started. This timer is used to create a maximum time in which the microprocessor will wait for a pulse signal. Next, the algorithm goes to the step indicated at 66.

At 66, a check is made as to whether a pulse signal has been received from the flow meter. If not, the algorithm goes to the step indicated at 68. If a pulse has been received at 66, WAIT is set to false and at step 70 a check is made as to whether SWITCH is true. If it is, Vol 1 is incremented. If it is not, Vol 2 is incremented. In either case, the algorithm then goes back to step 66. In the alternative embodiment of FIG. 5 utilizing the flow direction sensor switches 51 and 53, no SWITCH variable is needed for the algorithm. In this embodiment the microprocessor may check the signal being received from the flow direction sensors 51 and 53 and then increment Vol 1 if the user is inhaling or Vol 2 if he is exhaling. Similarly, when separate flow meters are used to sense inhaled and exhaled volume, as in the embodiment of FIG. 4, the algorithm is appropriately modified.

At 68, a check is made as to whether both WAIT is true and the wait timer has not expired. If either of these conditions are not true, the algorithm goes to the step indicated at 72. Else, the algorithm continues at step 66.

At 72, SWITCH is complemented. Next, a check is made as to whether SWITCH is set to true. If so, the algorithm goes to the step indicated at 74. If SWITCH is false, the algorithm goes back to step 64.

At 74, a check is made as to whether either the interval timer has expired or WAIT is set to true. IF either of these conditions is true, the algorithm continues to the step indicated at 76. Else, it goes back to step 64.

At 76, the absolute value of the difference between Vol 1 and Vol 2 (the difference between exhaled and inhaled oxygen volumes) is stored in the current register. Next, a check is made as to whether the main timer has expired. If so, the algorithm continues to the step indicated at 78. Else, the algorithm goes back to step 60 and goes through the routine another time, loading the integrals of the volume signals for the next interval of time (preferably one minute) into the next register. At 78, the LED signal light 26 of FIG. 1 is illuminated in order to indicate to the user that he may quit at any time. The microprocessor senses that the user quit when no pulse signal is received from the flow meter for an entire period of the wait timer.

Next, a check is made as to whether WAIT is set to true. If so, the algorithm continues at the step indicated at 80. IF WAIT is false, the algorithm goes back to step 60.

At 80, the five registers are summed together to arrive at an integral of the difference between exhaled and inhaled oxygen volumes over the latest portions of the test. Next, the volume of the oxygen inspired per minute, $VO_2$, is displayed on the digital display 28 of the microprocessor unit 20, as shown in FIG. 1. Finally, the sum is multiplied by a factor to arrive at the number of kilocalories that the subject expends during a 24 hour period. This factor is arrived at as follows: Approximately 5 kilocalories are expended for every 1 liter of oxygen consumed in a minute. In the preferred embodiment of the present invention, the volumes of oxygen are measured in millimeters. Therefore, the number of kilocalories expended over a 24 hour period = $VO_2$ * 1 liter/1000 ml * 5 kcals/liters/minute * 60 minutes/hour * 24 hours/day. This result is displayed on the digital display 29 of the unit 20, and a report of the test results is outputted to the printer 43, as shown in FIG. 2. An alternative algorithm may also display the volume of oxygen inspired per minute after the main timer has expired and continue to update it after each interval period.

The disclosure of the algorithm depicted in FIG. 3 is not intended to limit the present invention. Many different algorithms may be implemented to achieve the same results. For the purposes of illustration, well-known housekeeping functions, such as error checking features, were omitted from the algorithm of FIG. 3.

Figure 4:
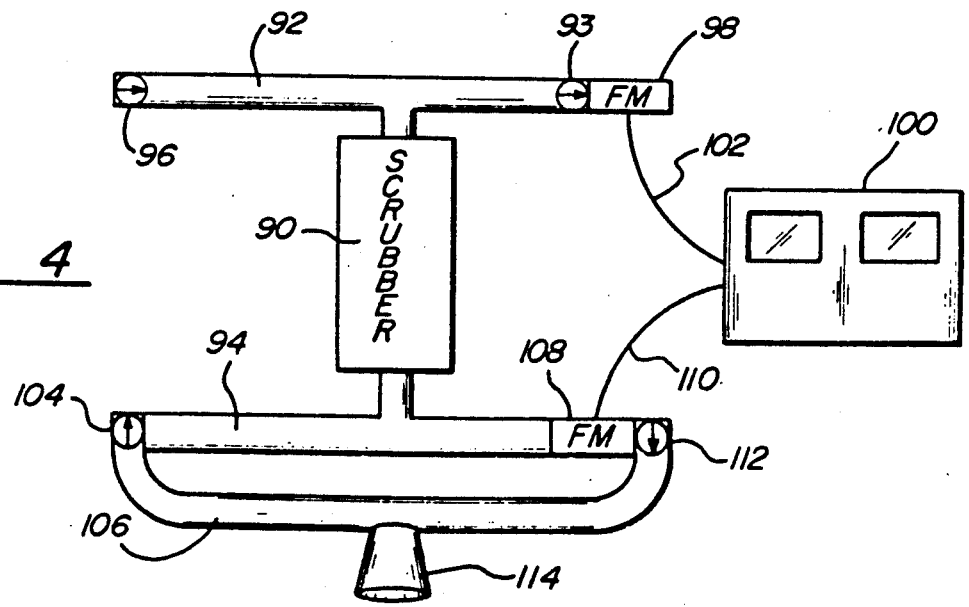
FIG. 4 is a schematic illustration of an alternative embodiment of the invention employing separate flow sensors for inhaled and exhaled gas.

FIG. 4 depicts an alternative embodiment of the present invention that includes two flow meters. This embodiment utilizes a carbon dioxide scrubber 90 that is connected at one end to a conduit 92, and at the opposite end to a conduit 94. Conduit 92 is connected to a one-way valve 96 at one of its ends. The valve 96 allows air to pass from the atmosphere into conduit 92. The other end of conduit 92 is connected to a flow meter 98. A one-way valve 93 is disposed between the conduit 92 and the meter 98 that allows air to flow from the conduit to the flow meter. The meter 98 is connected to the microprocessor unit 100 via connection line 102. Air may pass from conduit 92, through flow meter 98, and exit to the atmosphere.

Conduit 94 is connected at one end to a one-way valve 104. The opposite end of valve 104 is connected to a conduit 106. Valve 104 allows for the passage of air from the conduit 106 into the conduit 94. The opposite end of conduit 94 is connected to a flow meter 108. Flow meter 108 is connected to the microprocessor unit 100 via connection line 110. The end of the flow meter 108 opposite the end connected to conduit 94 is connected to a one-way valve 112. The valve 112 connects the meter 108 to the end of conduit 106 that is opposite the end connected to valve 104. Valve 112 allows for the passage of air from meter 108 into conduit 106.

Conduit 106 is also directly connected to a mouthpiece, indicated at 114. The mouthpiece is removably attached to the conduit. Furthermore, the scrubber 90 is also removably attached to the system and is preferably a large one of the type that may be used a plurality of times before becoming saturated with carbon dioxide.

The system operates as follows: When a user inhales through mouthpiece 114, atmospheric air is drawn into valve 96, through conduit 92, through the scrubber 90, into conduit 94, through flow meter 108, through valve 112, into conduit 106, through the mouthpiece and into the user's lungs. Exhaled air passes through the mouthpiece, into conduit 106, through valve 104, into conduit 94, through the scrubber 90, into conduit 92, through valve 93 and through flow meter 98, exiting to the atmosphere.

This embodiment requires calibration of the two flow meters in the manner previously noted and, obviously, a different algorithm for the operation of the microprocessor than the one shown in FIG. 3. In this embodiment, the microprocessor need not distinguish inhalation pulse signals from exhalation signals because it receives two inputs, one for each flow meter. The algorithm may also be further extended to include means for keeping track of the number of times that the installed scrubber is used, and then indicating to the user that the system is due for a new scrubber after a certain limit is passed.

Figure 6:
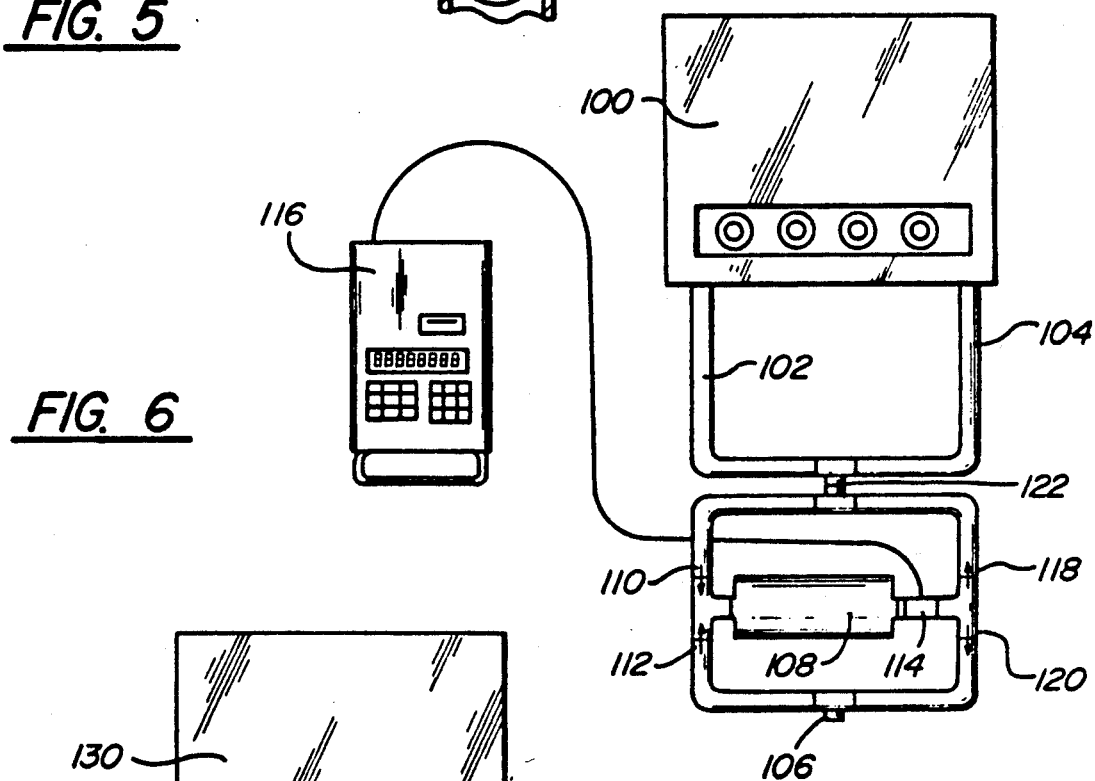
FIG. 6 is a schematic illustration of an alternative embodiment of the invention designed for use with a positive pressure respiratory ventilator.

FIG. 6 illustrates an embodiment of the invention useful with a respiratory ventilator 100 having a conduit 102 for inspired air and a conduit 104 for expired air. The ventilator 100 may of the positive pressure ventilation type which incorporates a sensor (not shown) either in the line 102 or the line 104 to control the ventilator to provide a positive pressure outflow through line 102 to force breathing of the patient. Rather than a mouthpiece or a mask, the embodiment of FIG. 6 employs a connector 106 adapted to be connected to an endotracheal tube passed through the patient's throat. The indirect calorimeter is otherwise the same as that of FIG. 2 with a scrubber 108 receiving either inhaled gas through a valve 110 or exhaled gas through one-way valve 112. The scrubber passes its output through a single flow meter 114 which is connected to a microprocessor and display unit 116. A pair of one-way valves 118 and 120 direct the gaseous output from the flow meter either to the patient on inspiration, or back to the patient on expiration. Both inspired and expired gasses are exchanged between the calorimeter and the ventilator through the connection 122.

The calorimeter is thus transparent to the ventilator, that is the ventilator operates as if it were connected directly to an endotracheal tube rather than indirectly to that tube through the calorimeter.

Figure 7:
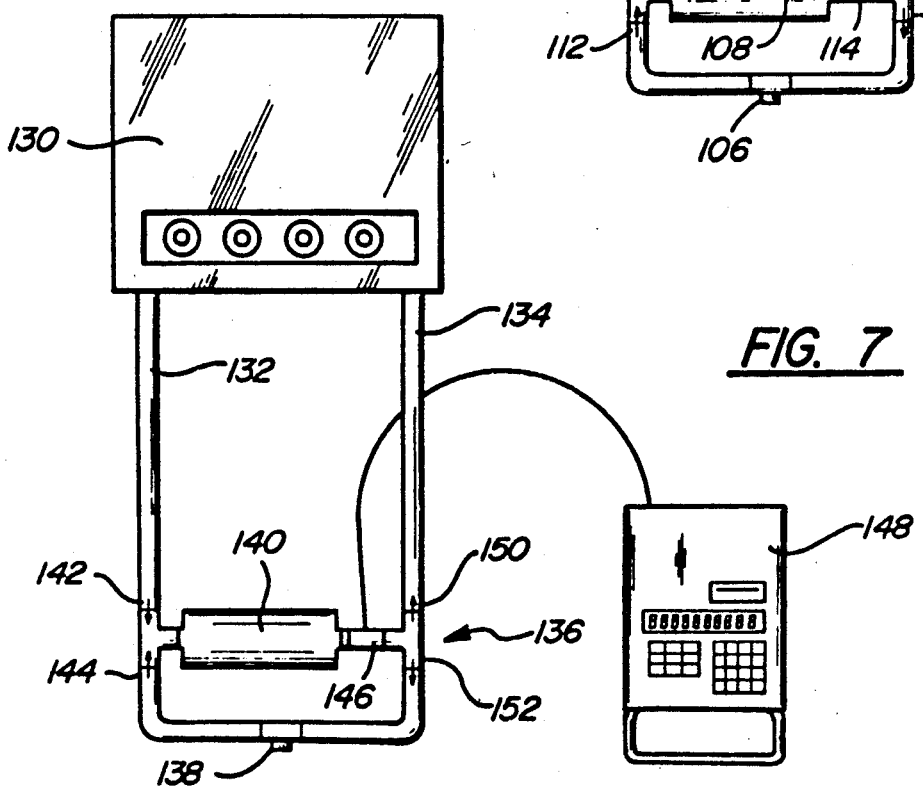
FIG. 7 is a schematic illustration of another alternative embodiment of the invention also designed for use with a respiratory ventilator.

Another alternative embodiment of the invention suitable for use with a positive pressure ventilator 130 of the type having separated inspiratory tubing 132 and expiratory tubing 134 is illustrated in FIG. 7. The indirect calorimeter, generally indicated 136, is substantially identical to that of FIG. 2 other than in providing a connection 138 for an endotracheal tube rather than the mouthpiece 12 of FIG. 2. The inspiratory tubing output of the ventilator 132 is passed to $CO_2$ scrubber 140 through a one-way valve 142 forming part of the calorimeter. Scrubber 140 also receives expired gases from the patient through a one-way valve 144. The output of the scrubber is passed through a flow meter 146 which provides an electrical output to a microprocessor and display unit 148. The gaseous outputs of the flow meter are either provided to the expiratory tubing 134 through a one-way valve 150 during exhalation or to the patient through a one-way valve 152 during inhalation.

This arrangement is suitable for use with mechanical ventilators that do not assist the patient's breathing after sensing his initial direction of breathing.

Having thus described my invention, I claim:

1. An indirect calorimeter operative to measure the respiratory oxygen consumption from respiratory gases per unit time of a subject, comprising:
   a respiratory connector operative to be supported in contact with the subject so as to pass said respiratory gases as the subject breathes into said respiratory connector;
   a scrubber having a gas inlet and a gas outlet and constructed to absorb carbon dioxide from said respiratory gases passing between its inlet and outlet;
   flow meter means operatively connected to said respiratory connector for generating signals as a function of the gas volume of said gases passed through said meter means;
   valves and conduits interconnecting said respiratory connector, scrubber, and flow meter means, and constructed such that upon the subject inhaling, gas is caused to pass through the scrubber, then through the flow meter means, and then to the subject's respiratory system through the respiratory connector, and upon the subject exhaling to pass the exhaled gas from the respiratory connector first through scrubber, then through the flow meter means;
   means for receiving the resultant signals from the flow meter means and for generating a signal proportional to the integral of the differences between the inhaled and exhaled gas volumes over a period of time; and
   means for connecting said conduits to a mechanical ventilator so that the ventilator may provide respiratory gas to the calorimeter and receive exhaled gas from the calorimeter.

2. The indirect calorimeter of claim 1 wherein the mechanical ventilator includes a single passage adapted to pass both inflow to the ventilator and outflow from the ventilator and said means for connecting said conduits to said mechanical ventilator includes a single conduit interconnecting said single passage to said respiratory connector, scrubber, and flow meter means, and constructed to pass respiratory gasses through said single passage of the ventilator.

3. The indirect calorimeter of claim 1 wherein said ventilator includes a first tube for passing gasses to be inhaled by the subject and a second tube to pass gasses exhaled by the subject, and said first and second tubes constructed to connect to separate sections of said conduits of the indirect calorimeter interconnecting said respiratory connector, scrubber and flow meter means.

4. The indirect calorimeter of claim 3 including a first one-way valve means for interconnecting said first tube of the ventilator with the conduits of the indirect calorimeter and a second one-way valve means for interconnecting the second tube of the ventilator to the indirect calorimeter.

5. The indirect calorimeter of claim 1 wherein said conduits have disposed therein a first pair of valves operably connected to said inlet side of the scrubber and adapted to connect the scrubber to a respiratory connector and a second pair of valves operably connected to said outlet side of the scrubber and adapted to connect the scrubber to a source and sump of respiratory oxygen.

* * * * *

UNITED STATES PATENT AND TRADEMARK OFFICE
CERTIFICATE OF CORRECTION

PATENT NO. : 5,038,792

DATED : August 13, 1991

INVENTOR(S) : James R. Mault

It is certified that error appears in the above-identified patent and that said Letters Patent is hereby corrected as shown below:

Title Page:
Under "Related U.S. Application Data" (63), Please delete "491,180 and insert -- 4,917,108 --.

Signed and Sealed this

Thirteenth Day of April, 1993

Attest:

STEPHEN G. KUNIN

*Attesting Officer*            *Acting Commissioner of Patents and Trademarks*